United States Patent
Toller et al.

(10) Patent No.: US 8,156,811 B2
(45) Date of Patent: Apr. 17, 2012

(54) APPARATUS AND METHOD FOR NON-DESTRUCTIVE TESTING

(75) Inventors: Steven M. Toller, Dublin, OH (US);
Craig T. Walters, Powell, OH (US)

(73) Assignee: LSP Technologies, Inc., Dublin, OH (US)

(*) Notice: Subject to any disclaimer, the term of this patent is extended or adjusted under 35 U.S.C. 154(b) by 526 days.

(21) Appl. No.: 11/227,745

(22) Filed: Sep. 15, 2005

(65) Prior Publication Data
US 2008/0257048 A1    Oct. 23, 2008

(51) Int. Cl.
*G01M 7/00*    (2006.01)
(52) U.S. Cl. .................. 73/588; 73/801; 73/842
(58) Field of Classification Search .......... 73/588, 73/789, 801, 815, 827
See application file for complete search history.

(56) References Cited

U.S. PATENT DOCUMENTS

| | | | | |
|---|---|---|---|---|
| 2,694,924 A | * | 11/1954 | Matlock et al. ................. 73/37 |
| 3,986,391 A | * | 10/1976 | Vahaviolos ..................... 73/781 |
| 4,004,456 A | * | 1/1977 | Vahaviolos ..................... 73/801 |
| 4,090,400 A | * | 5/1978 | Vahaviolos ..................... 73/801 |
| 4,207,771 A | * | 6/1980 | Carlos et al. ................... 73/587 |
| 4,401,477 A | * | 8/1983 | Clauer et al. ................... 148/525 |
| 4,545,018 A | * | 10/1985 | Clements et al. ............. 700/166 |
| 4,824,250 A | * | 4/1989 | Newman ....................... 356/502 |
| 4,838,085 A | * | 6/1989 | Pellerin et al. ................. 73/597 |
| 4,901,357 A | * | 2/1990 | Albright ........................ 381/400 |
| 5,127,019 A | * | 6/1992 | Epstein et al. ................. 372/108 |
| 5,172,019 A | | 12/1992 | Naylor et al. |
| 5,269,778 A | * | 12/1993 | Rink et al. .................... 606/12 |
| 5,473,315 A | * | 12/1995 | Holroyd ....................... 340/683 |
| 5,572,016 A | * | 11/1996 | Wood et al. ................ 250/227.15 |
| 5,698,787 A | * | 12/1997 | Parzuchowski et al. ........ 73/643 |
| 5,729,012 A | * | 3/1998 | Wood et al. ................ 250/227.15 |
| 5,803,965 A | * | 9/1998 | Yoon ............................. 117/4 |
| 5,895,589 A | * | 4/1999 | Rogers et al. ............ 219/121.76 |
| 5,965,877 A | * | 10/1999 | Wood et al. ................ 250/227.15 |
| 6,008,887 A | * | 12/1999 | Klein et al. ................. 356/28.5 |
| 6,238,187 B1 | * | 5/2001 | Dulaney et al. ............ 416/241 R |
| 6,263,737 B1 | * | 7/2001 | Schoess ........................ 73/583 |
| 6,282,964 B1 | * | 9/2001 | Hancock et al. ................ 73/622 |
| 6,288,358 B1 | * | 9/2001 | Dulaney et al. ............ 219/121.6 |
| 6,373,876 B1 | * | 4/2002 | Dulaney et al. ................. 372/98 |

(Continued)

FOREIGN PATENT DOCUMENTS
GB    2225427 A    5/1990

*Primary Examiner* — Hezron E Williams
*Assistant Examiner* — Samir M Shah
(74) *Attorney, Agent, or Firm* — Benjamin E. Kern

(57) ABSTRACT

A diagnostic means to enable real-time inspection of bonded structures. The disclosed apparatus detects bond failure stress waves on-axis from the front side (beam application side). Pi-box and pi-rail EMAT gauges can be used with the disclosed apparatus. An inductively coupled EMAT may also be employed. An improved means to remotely deliver an interrogating laser beam to a surface is provided. The process head may utilize a water column or a water film. The water film process head may include the use of either a single water film or two spaced apart water films. The disclosed apparatus can be used with bonded composite structures, bonded structures using various materials, and to determine the dynamic strength of unbonded solid materials. The apparatus may also be used in other applications that require remote flexible delivery of a localized stress wave to a material and/or diagnosis of the resultant stress waves.

15 Claims, 11 Drawing Sheets

U.S. PATENT DOCUMENTS

| | | |
|---|---|---|
| 6,512,584 B1 * | 1/2003 | O'Loughlin et al. ......... 356/388 |
| 6,554,921 B2 * | 4/2003 | Sokol et al. .................. 148/508 |
| 6,558,493 B1 * | 5/2003 | Ledger et al. ................... 156/98 |
| 6,622,568 B2 * | 9/2003 | Nelson et al. .................. 73/800 |
| 6,716,297 B2 * | 4/2004 | Essig et al. .................... 156/705 |
| 6,759,626 B2 * | 7/2004 | Clauer et al. ............... 219/121.6 |
| 6,848,321 B2 * | 2/2005 | Bossi et al. ..................... 73/842 |
| 6,945,114 B2 * | 9/2005 | Kenderian et al. ............. 73/643 |
| 6,983,660 B2 * | 1/2006 | Kwon ............................. 73/806 |
| 7,107,118 B2 * | 9/2006 | Orozco et al. ................ 700/166 |
| 7,131,331 B2 * | 11/2006 | Bates .............................. 73/589 |
| 7,253,908 B2 * | 8/2007 | Vaccaro et al. ............... 356/607 |
| 7,270,004 B2 * | 9/2007 | Dickinson et al. .............. 73/602 |
| 7,574,916 B2 * | 8/2009 | Tillotson ......................... 73/588 |
| 7,765,861 B2 * | 8/2010 | Jacquemin .................. 73/150 A |
| 7,770,454 B2 * | 8/2010 | Sokol et al. ..................... 73/588 |
| 2002/0112548 A1 * | 8/2002 | Dong et al. ..................... 73/850 |
| 2005/0120803 A1 * | 6/2005 | Sokol et al. ..................... 73/801 |
| 2005/0139006 A1 * | 6/2005 | Lorraine et al. ................ 73/597 |

* cited by examiner

APPARATUS AND METHOD FOR NON-DESTRUCTIVE TESTING

This application claims the benefit of prior filed U.S. Provisional Application No. 60/610,102 filed Sep. 15, 2004, in the name of the above named inventors, the disclosure of which is incorporated herein by reference thereto.

BACKGROUND OF THE INVENTION

1. Field of the Invention

The present invention relates to non-destructive inspection of composite structures.

2. Description of the Related Art

A critical need in the aircraft industry is the non-destructive inspection (NDI) of composite structures assembled with adhesive bonds. The typical means of testing bonded structures is a destructive proof test that may validate an assembly process, but does not prove that any given assembly is sufficiently strong to have a high probability of not failing in service.

In particular, it is of interest to find weakly bonded layers in multi-layer carbon-fiber/resin-matrix skins and internal members. These weak bond areas are not observable with conventional ultrasound or thermal techniques because the bond between layers, while weak, is intact or in contact and no delamination area exists that would be visible to standard inspection techniques. These defective bonds could arise from (1) improper preparation of the surfaces to be bonded; (2) improper mixing, application, and/or curing of the adhesive; or (3) contamination of the surfaces before bonding. In the past, electron beam pulses have been used to deposit energy in depth in a composite structure on a time scale that is short compared to the acoustic transit time through the thickness of the material. This energy deposition results in a release wave propagating into the material from both surfaces. When the release waves meet they produce a tensile stress which can be used to test the strength of the bond at that point in the material. Unfortunately, the electron beam generator is massive, therefore not portable, and the output beam cannot be conveniently moved around the surface of an aircraft to test the skin or other structural members.

Patent Application No. US 2002/0129659 A1 and US 2003/0079552 A1 provide examples of known methods and apparatus.

SUMMARY OF THE INVENTION

The present invention provides a diagnostic means to enable real-time inspection of bonded structures. This invention provides an improved means to detect bond failure stress waves on-axis from the front side (beam application side). The present invention also provides an improved means to remotely deliver an interrogating laser beam to a surface. The scope of the invention is not limited to bonded composite structures alone, but is applicable to bonded structures using various materials and may be used to determine the dynamic strength of unbonded solid materials themselves. Furthermore, the apparatus may be used in other applications that require remote flexible delivery of a localized stress wave to a material and/or diagnosis of the resultant stress waves.

BRIEF DESCRIPTION OF THE DRAWINGS

The above mentioned and other features and objects of this invention, and the manner of attaining them, will become more apparent and the invention itself will be better understood by reference to the following description of the invention taken in conjunction with the accompanying drawings, wherein.

Although the exemplification set out herein illustrates embodiments of the invention, the embodiments disclosed below are not intended to be exhaustive or to be construed as limiting the scope of the invention to the precise forms disclosed.

DETAILED DESCRIPTION OF THE INVENTION

The use of short laser pulses has been demonstrated to be an effective means of generating stress waves for proof testing of adhesive bonds in composite structures. The process of laser bond inspection (LBI) entails deposition of laser energy at the front surface of a structure (which generates a compressive stress wave), propagation of the stress wave to the back surface or first free surface, reflection of the compressive stress wave to form a tensile wave, and breaking of weak bonds in the structure with the tensile wave as it travels back toward the front surface. For practical implementation of this process in a production environment, a tool must be moved along the structure to be tested and a test result for the bond must be reported at each inspection point.

Figure 1:
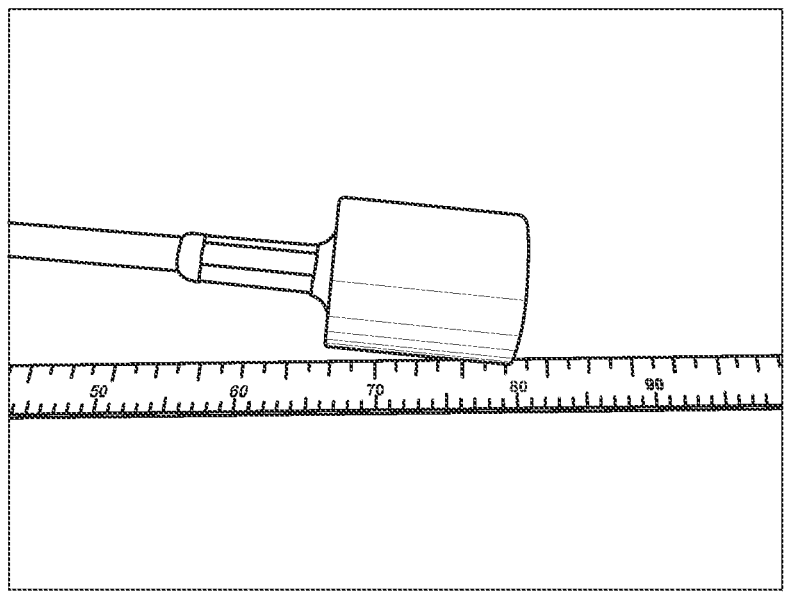
FIG. 1 is a view of a non-contact compact EMAT gauge for sensing surface motion.

Process head concepts have been developed and demonstrated for delivery of the laser beam pulses to the surface to be tested. Sensors have also been developed for indicating whether or not the bond failed under the action of the interrogating laser pulse. For the case where the back surface of the bonded structure is accessible, a velocity interferometer system for any reflector (VISAR) probe measurement of the back surface motion has been demonstrated to be effective in detecting signatures of failed bonds in a single-pulse real-time mode and in a probe-break-probe mode of inspection. In the latter case, a calibration signature is first obtained at low pulse fluence. An interrogation pulse is then delivered that has a fluence less than that required to break a good bond. If the bond is weak it will break and will provide a different back-surface-motion signature when probed with a third pulse at the same fluence as the initial probe pulse. For uniform thickness materials, the initial probe pulse may only be required for the first inspection point in a series. For strong bond breaks, the signature for the interrogating pulse clearly shows the break. For reliably finding threshold breaks, the probe-break-probe mode will likely be required. While the VISAR probe could be used in a production laser bond inspection device (LBID), a much more cost effective approach is the electromagnetic acoustic transducer (EMAT) gauge. FIG. 1 shows an EMAT gauge for probing the back surface of a structure when it is accessible. This non-contact gauge (EMAT5) is very compact, self-contained, and provides surface motion signatures with fidelity close to that provided by the more complex VISAR system. As with the VISAR probe, the surface motion detected by the EMAT gauge is directly related to the internal stress wave intensity and is a good indicator of the integrity of the material traversed by the wave.

There are many cases where the back surface of the structure to be inspected is not accessible to sensors. One example is low density "honeycomb" core structure bonded between the upstanding legs of a pi clip. In this case, the laser pulse is applied to the pi leg and the stress wave travels through the leg/adhesive/core-face-sheet stack. The stress wave reflection occurs at the back surface of the face sheet (the interface between the face sheet and the honeycomb core material). This surface is not available for placement of surface motion probes.

A critical problem in LBI is to be able to detect the bond or material failure in real time from the front (accessible) side.

Initial attempts at front-surface motion sensing of bond break signatures employed the EMAT5 gauge in an off-axis location and indicated that strong bond breaks could be detectable with this approach. However, surface motion at the off-axis location will not be very sensitive to threshold bond break conditions. For this reason, on-axis approaches to front-surface motion sensing have appeal. One approach is to miniaturize an EMAT structure similar to that shown in FIG. 1 above. The problem that arises is blocking of the main laser beam by the coil structure. An annular beam or double "D" beam pattern could accommodate such a coil, but the structure would have to be relatively small (1-2 mm). Annular and double "D" patterns have been shown to be effective for LBI at the expense of available beam energy or complex optics. The simplest approach for an on-axis front-surface EMAT gauge is the direct-read surface-mounted gauge.

Figure 2:
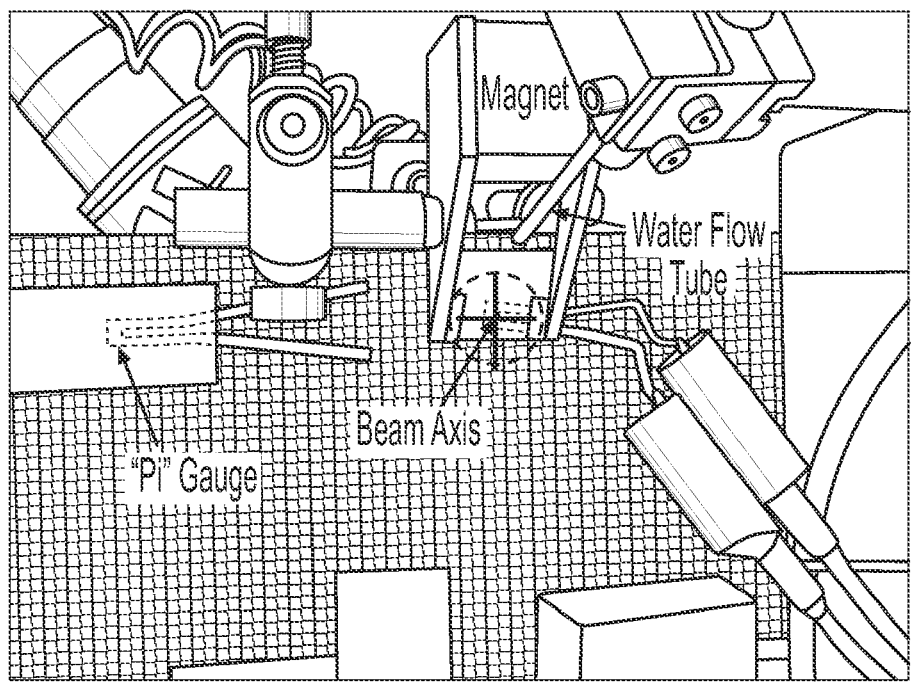
FIG. 2 is a view of a test setup for front-surface on-axis direct-read EMAT gauge.

FIG. 2 presents a photograph of a direct read EMAT gauge. This gauge, designated a "pi" gauge because of the shape, consists of a conducting foil pattern adhered to the surface and an external magnetic field provided by a permanent magnet and pole pieces. The vertical strip in the pattern is placed at the center of the laser beam and the horizontal strips provide leads for measuring the gauge signal current. This EMAT gauge was used successfully to detect bond failure.

Although this approach works, it has the disadvantage that it is difficult to make reliable electrical contact with the gauge leads in the production inspection environment. One approach for implementation is the use of commercial spring-loaded waffle-pattern contacts that would be incorporated in the process head. As the head would descend on a pre-placed conductor pattern, contact would be made with the sensor leads.

An improvement on the direct contact approach to readout of the gauge signal would employ inductive coupling to the voltage reading instrumentation rather than conductive coupling. In this approach, the pi gauge leads would be closed on themselves forming a conducting loop. An appropriate adjacent coil will sense the loop current by induction without the need for direct electrical contact.

Tests were conducted with two different pi gauge geometries and several pickup coils as discussed below.

Pi-Box EMAT Gauge

Figure 3:
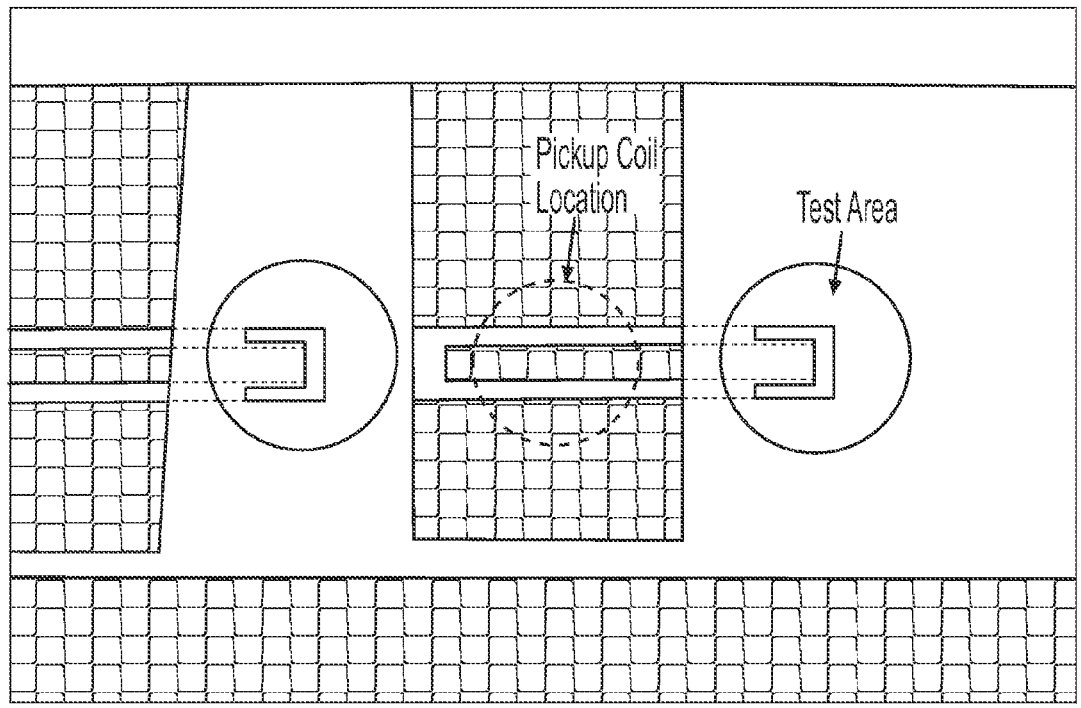
FIG. 3 is a view of two pi-box EMAT gauges mounted on a composite sample (after test).

The simplest form of closed loop pi gauge was an extension of the previous style pi gauge with the two leads connected by a strip at the end opposite the sensing end of the gauge. This approach forms a box shaped loop referred to as a "pi-box". This geometry is shown in the photograph of FIG. 3. In the figure, the sensing portion of the gauge that is in the magnetic field is the vertical strip at the far right of the photograph (in the laser interaction area). The current loop is closed by the vertical strip near the center of the photograph. When a coil is placed next to the surface in the area indicated by the dashed white line, current flowing in the loop in the surface conducting pattern induces a current in the coil without the need for electrical contact.

Figure 4:
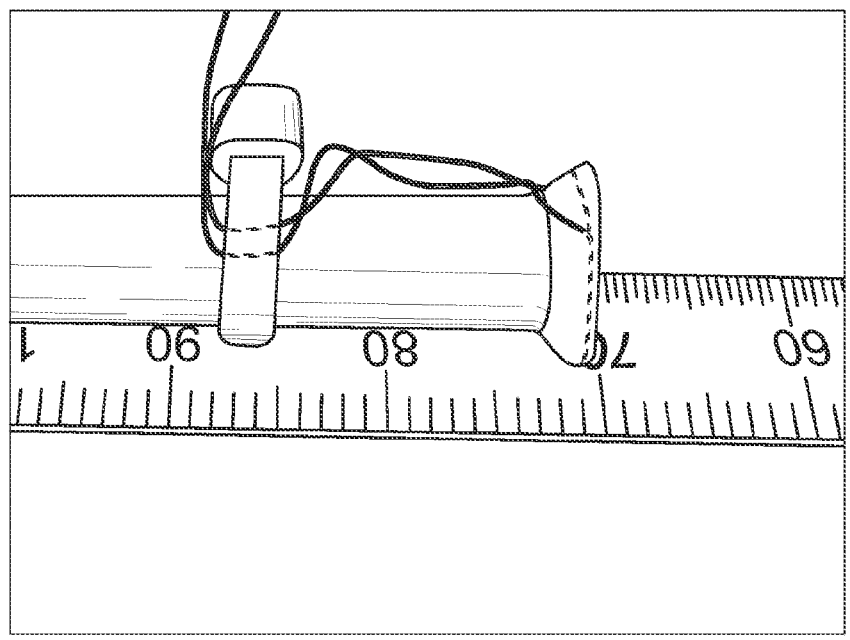
FIG. 4 is a view of a pickup coil for inductively coupled surface EMAT gauge.

The pi-gauge patterns were formed by cutting adhesive backed aluminum tape (2-mil thick) with a razor blade and mounting them directly on the composite surface. The beam interaction area was coated with the standard flat black absorbing paint. Prototype pickup coils were fabricated by winding coils of 34 Gauge copper magnet wire on a nylon screw mandrel. Coils with 5, 7, 10, 20, and 40 turns were prepared. FIG. 4 presents a close-up view of a typical pickup coil. The coil was placed adjacent to the pi-box in the area indicated in FIG. 3.

Figure 5:
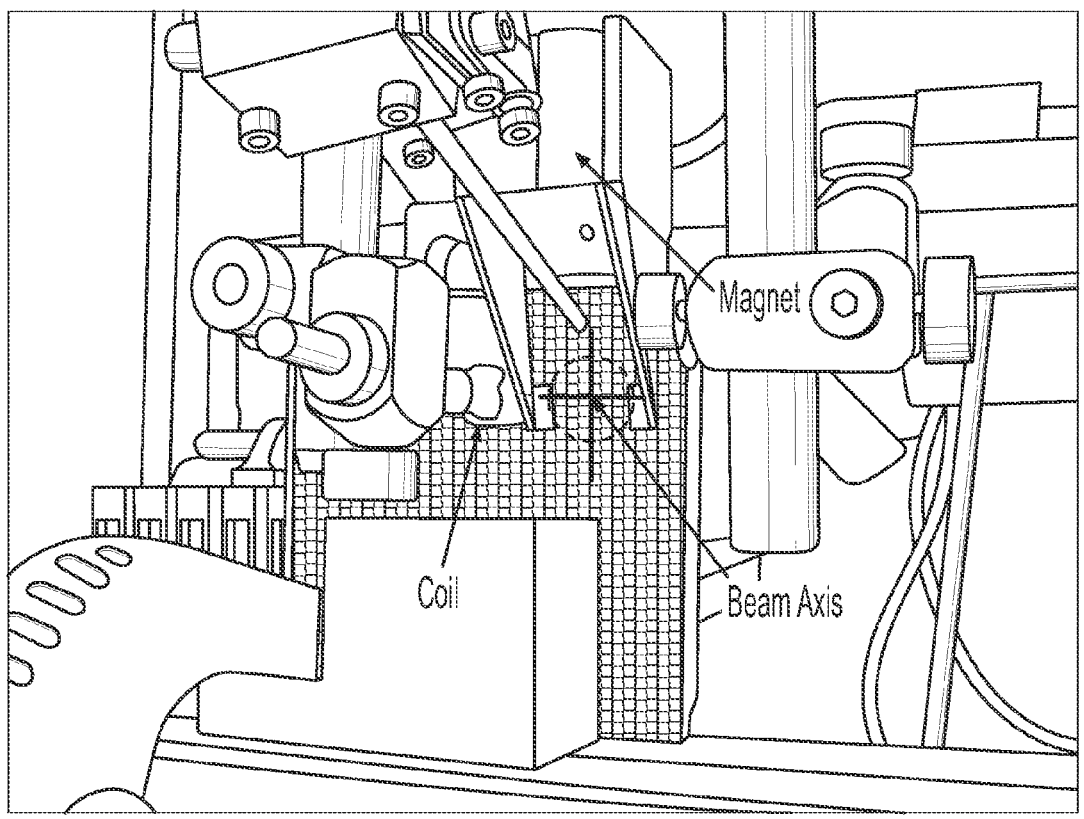
FIG. 5 is a view of a test setup for measurement of surface motion with inductively coupled EMAT.

The magnetic field for the gauge was supplied by the EMAT2 permanent magnet and pole piece structure. This magnet provides a field that is perpendicular to the sensing strip of the foil pattern (1 mm by 3 mm vertical strip to the right of FIG. 3) and parallel to the substrate surface. The horizontal strips are parallel to the magnetic field and surface motion in those regions do not contribute to signal current. The closing strip for the loop is well outside of the magnetic field concentrated by the pole pieces and, therefore, does not contribute to the signal. The long loop allows the pickup coil to be placed out of the way of the laser beam and the pole pieces. The whole assembly is shown in FIG. 5.

Pi-Rail EMAT Gauge

Figure 6:
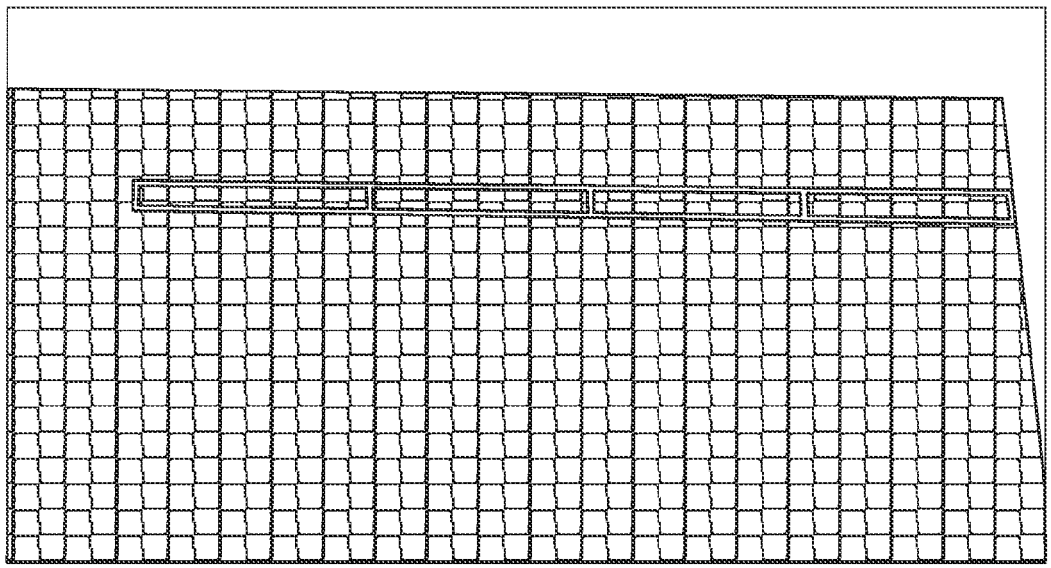
FIG. 6 is a view of a pi-rail EMAT pattern on a composite surface prior to painting.

The initial tests with the pi-box EMAT gauge were successful as discussed below. It is envisioned that a small adhesive patch having the box pattern could be fabricated by mass production techniques. An inspection technician could apply such a patch at any desired inspection location and then use the LBI process to interrogate the bond under that location. A natural extension of the concept was developed when considering the problem of inspection of a long joint along a linear path at regular intervals. For this case, the pi-rail pattern approach was conceived wherein two foil "rails" would be connected at regular intervals (e.g., 1-inch spacing) with 1-mm wide bars that would serve as motion sensing conductors and as loop closing conductors. The concept is illustrated in the photo of FIG. 6 which shows a pi-rail pattern of aluminum foil tape on a sample prior to painting. In this case, there are four cross strips spaced at 1-inch intervals which could serve as inspection points (the furthest strip to the right is too close to the edge to be of value). The major concern with this approach was the possibility that the extra conduction paths for signal current would decrease the useful signal level in the pickup coil. This proved not to be the case as shown below. Thus it is envisioned that a continuous adhesive-backed tape could be fabricated ("inspection tape") that could be laid down by the LBI operator prior to inspection of a linear joint structure. Marks on the tape would guide the operator where to place the process head. The tape could be removed and stored temporarily as a record of the locations inspected on the structure.

Test Results

Figure 7:
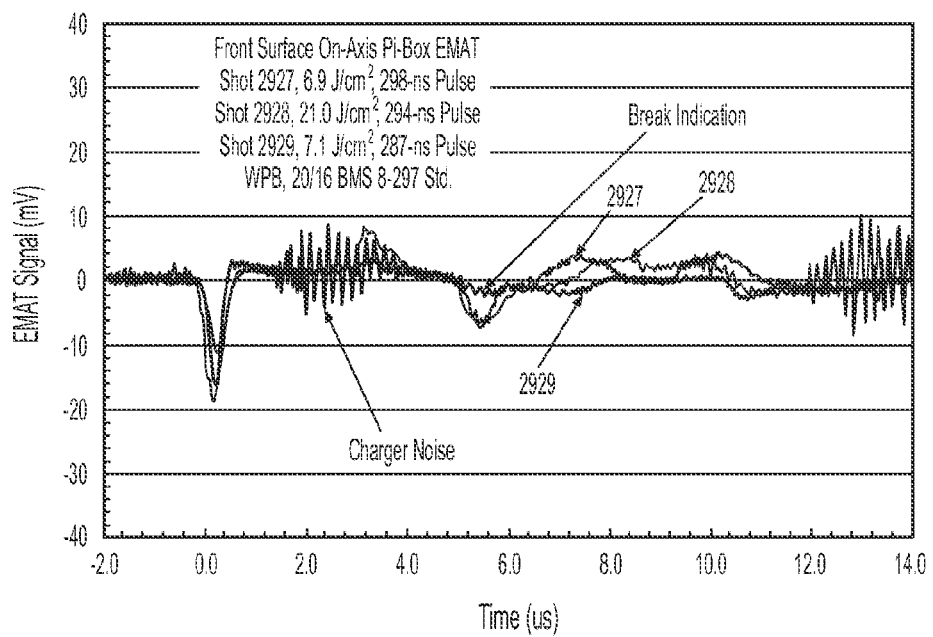
FIG. 7 is a chart illustrating an EMAT signal for 10-turn coil with pi-box conductor pattern.

The experimental arrangement shown in FIG. 5 was employed to test the effectiveness of the inductively coupled on-axis front-surface EMAT gauge concept. A ten-turn coil was used initially with the pi-box pattern to interrogate a 20-ply/16-ply BMS 8-297 composite coupon bonded with standard strength EA9394 paste adhesive and prepared with 80 grit blast. The coil leads were attached to a 50-ohm triax cable which was connected to an oscilloscope channel terminated in 50 ohms. The output of the ten-turn coil is plotted in FIG. 7 for three laser exposures on the same spot in a probe-break-probe inspection sequence. The 2927 trace presents the pre-probe signature for the sample and reflections from the back surface at 5.5 and 11 µs are clearly evident. The pre-probe test was followed by an interrogation pulse at a fluence designed to break the bond (2928 trace, 21 J/cm$^2$). The 2929 trace shows the EMAT record at the same spot for the post-probe test. As expected, the reflection from the back surface at 5.5 µs in this trace is almost gone entirely because the broken bond cannot transmit the tensile wave. These results confirmed that the inductive coupling concept is valid.

Several changes were made in the measurement to improve the signal-to-noise ratio. By increasing the number of turns in the receiver coil, the signal strength was increased significantly, although not linearly with turn count. The forty-turn coil gave the best performance, but the small improvement over the twenty-turn coil suggested the optimum turn count is in the twenty to forty range. Another improvement was the shielding of the receiver coil to eliminate the 6-MHz noise bursts emanating from the high voltage charger for the "D" laser amplifier heads. The improved receiver coil was used successfully with the pi-rail gauge pattern as discussed below.

Figure 8:
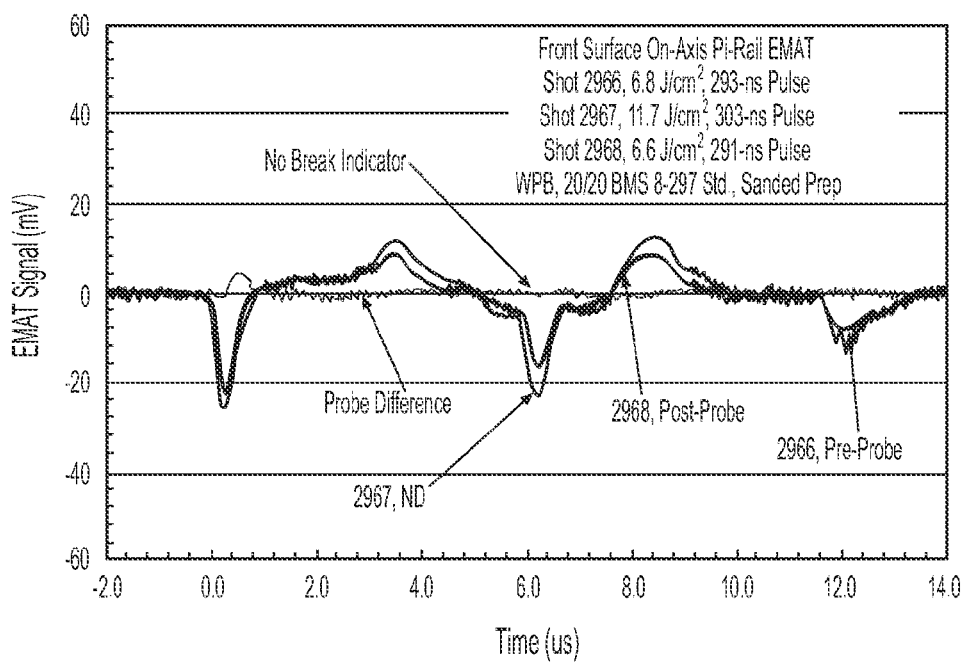
FIG. 8 is a chart illustrating a pi-rail EMAT signature below bond failure threshold in 20-ply/20-ply BMS 8-297.
Figure 9:
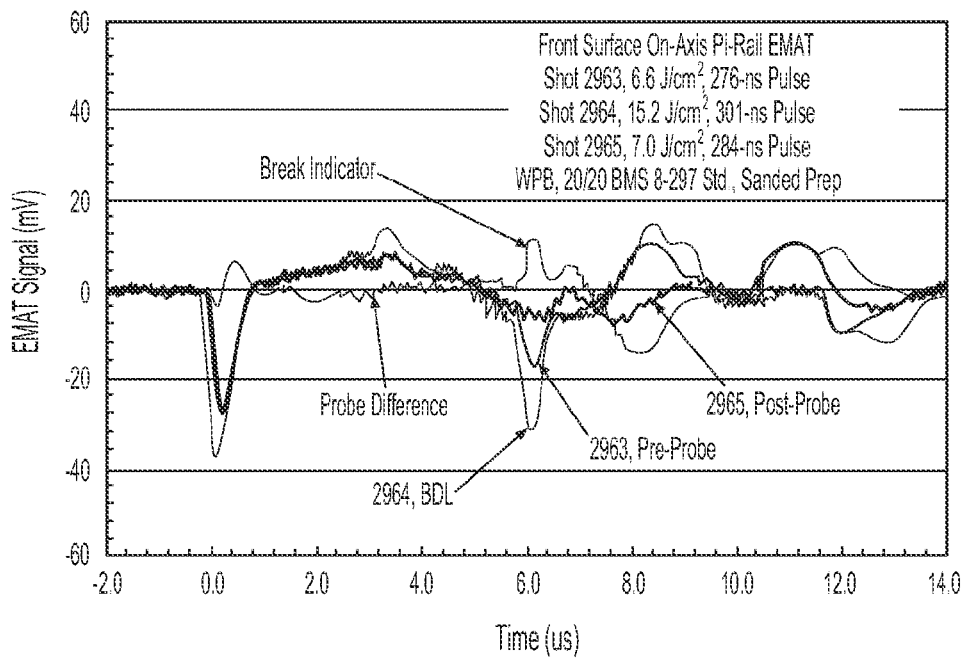
FIG. 9 is a chart illustrating a pi-rail EMAT signature just above bond failure threshold in 20-ply/20-ply BMS 8-297.
Figure 10:
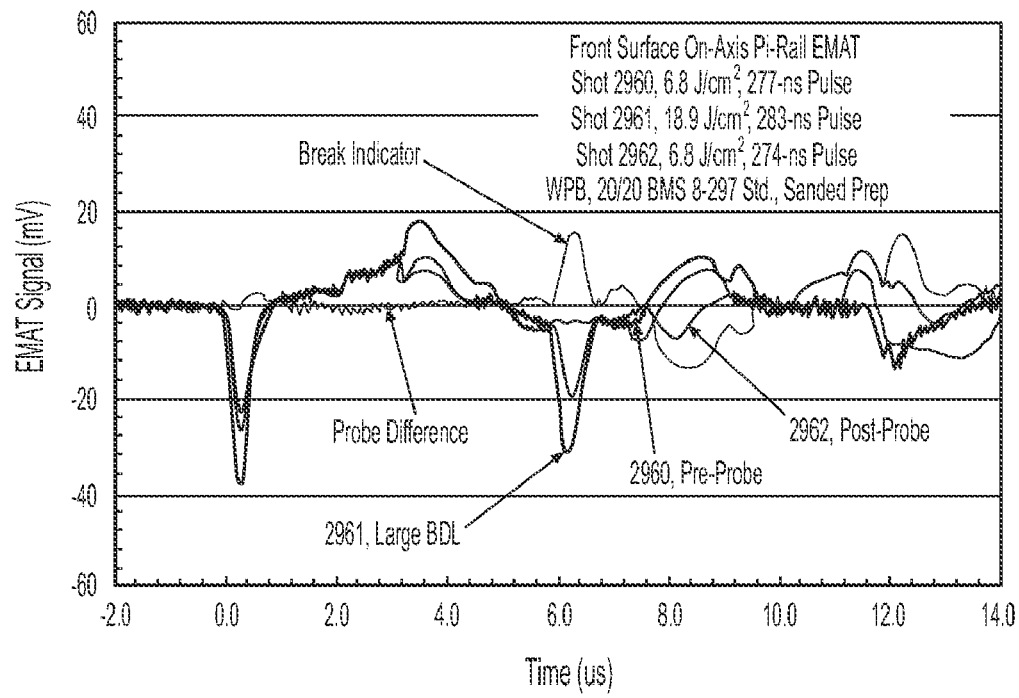
FIG. 10 is a chart illustrating a pi-rail EMAT signature well above bond failure threshold in 20-ply/20-ply BMS 8-297.

The pi-rail gauge pattern of FIG. 6 was used in a series of tests designed to test the effectiveness of the optimized inductively coupled EMAT concept in a practical inspection geometry for a linear inspection sequence. The pi-rail pattern was applied to a 20-ply/20-ply BMS 8-297 composite coupon bonded with standard strength EA9394 paste adhesive and sanded surface preparation. FIGS. 8, 9, and 10 present LBI results for three inspection points that received interrogation fluences below, just above, and well above the bond failure fluence level, respectively. The probe-break-probe mode of inspection was used at each inspection point.

In FIG. 8, the relatively dark 2966 and relatively light 2968 traces present the pre-probe and post-probe EMAT signatures of front-surface motion, respectively. The probe difference trace shows the difference between these two traces and serves as an indicator of bond change due to the interrogation pulse. For the interrogation fluence applied at this inspection point, the probe difference trace is nearly zero and it may be concluded that the bond did not break, in this case. The intact bond was confirmed by post-test UT of the coupon. FIG. 9 presents similar data for a second inspection point at which the imposed interrogation fluence was above the bond failure fluence. The deviation of the probe difference trace from zero is clearly evident. At 6 µs, the post-test probe senses very little of the tensile wave reflected from the back surface because the broken bond cannot support tension. Considerable deviation of the probe difference trace from zero is also seen well after 6 µs because of the general disruption of the stress wave propagation by the broken bond. At even higher interrogation pulse fluences, the probe difference trace shows even greater deviations from zero as shown in FIG. 10.

Figure 11:
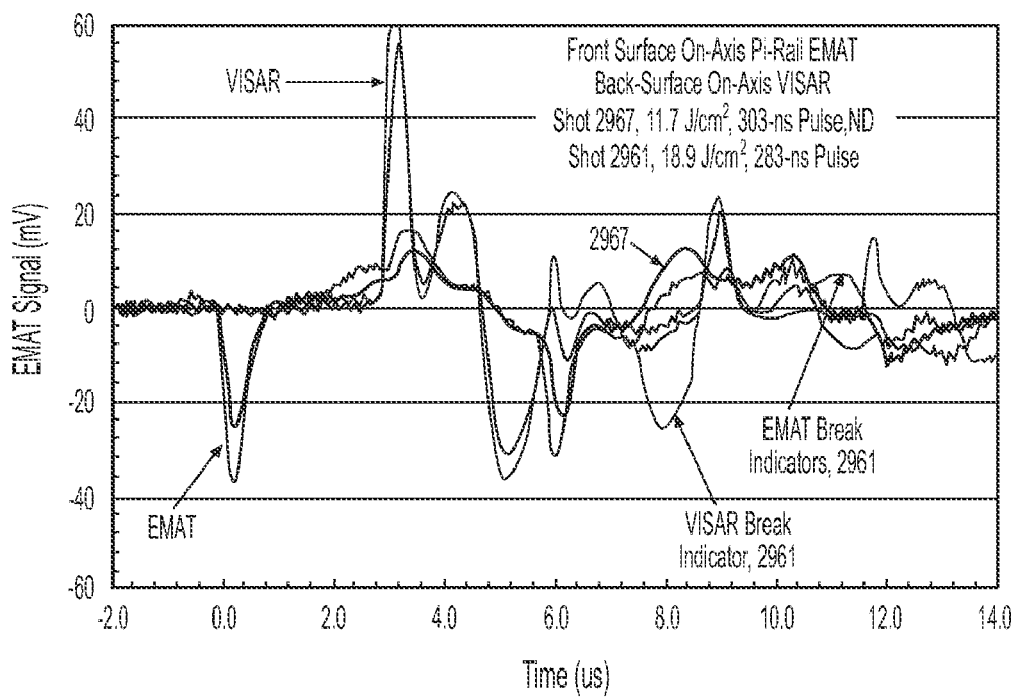
FIG. 11 is a chart illustrating real-time break indicators for back-surface VISAR and front-surface EMAT sensors.

While there are also some real-time indications of bond failure noted in the 2964 and 2961 traces in FIGS. 9 and 10, these are more subtle and may be difficult to detect in threshold bond failure cases. FIG. 11 presents both the front-surface EMAT signals and simultaneous back surface VISAR signals for the interrogation pulse in the no damage and strong bond failure case. The two traces identified by the term "VISAR" in the upper left portion of FIG. 11 graph the VISAR data and the characteristic signature of bond failure in 20-ply/20-ply material is noted in the 2961 VISAR trace at 8 µs. The two traces identified by the term "EMAT" in the lower left portion of FIG. 11 present the EMAT signals for the same tests and significant shape changes for the 2961 EMAT trace are noted at 11 and 13 µs. It is anticipated that for the most reliable sensing of bond failure, both the probe difference and real-time indicators will be applied in the bond assessment for LBI.

Figure 12:
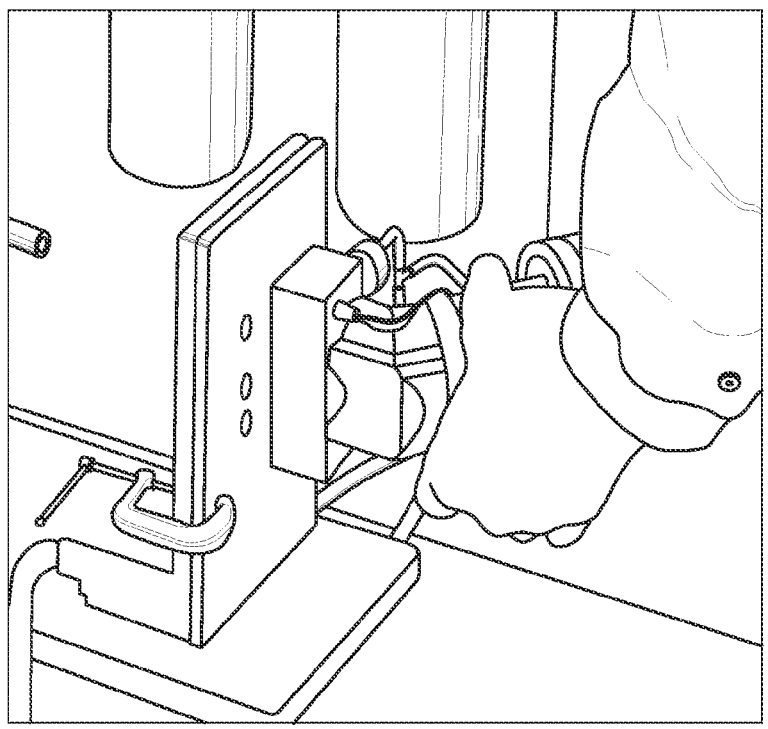
FIG. 12 is a view of a LBID water column process head (PH4).

Process head concepts for delivery of the laser beam pulses to the surface to be tested include a water column concept (PH4) and a water film concept (PH5). The water column concept (shown in FIG. 12) delivers the beam through a 28-cm long column of water that serves as the confining overlay for the laser beam interaction with the front surface of the material to be tested.

Features of the water column approach include:
final optical surface for beam delivery is immersed in water and is protected from paint debris by water flow;
laser beam scatter is well-confined;
acoustic noise emission is relatively low;
however, water column absorbs 50 percent of laser beam; and
design demonstrated to 15 J/cm$^2$ on work surface.

Figure 13:
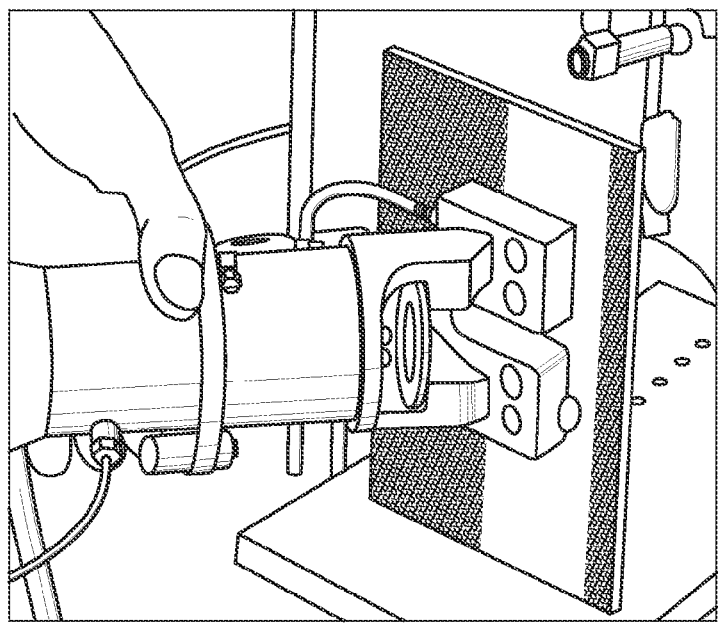
FIG. 13 is a view of a LIBID water film process head (PH5).

The PH4 process head will work well for many applications, however there will be applications, such as thick layer bonded structures, which will require larger fluence levels on the front surface. A second process head was successfully tested that permits much higher energy beams to be delivered reliably. This process head (PH5) employs a water film at the work surface to confine the surface vapor expansion and an air flow over a beam aperture to prevent water and paint debris from splashing onto the final optical surface of the beam delivery system. This process head is shown in FIG. 13.

Features of the water film approach include:
Strong air flow which keeps water and paint debris off final optic
Robust mechanical design
However, laser beam scatter not well-confined
Acoustic noise emission from surface vapor expansion and air flow require ear protection
Design demonstrated to 27 J/cm$^2$ on work surface (capable of 40 J/cm$^2$)

Short Water Column Concept

Figure 14:
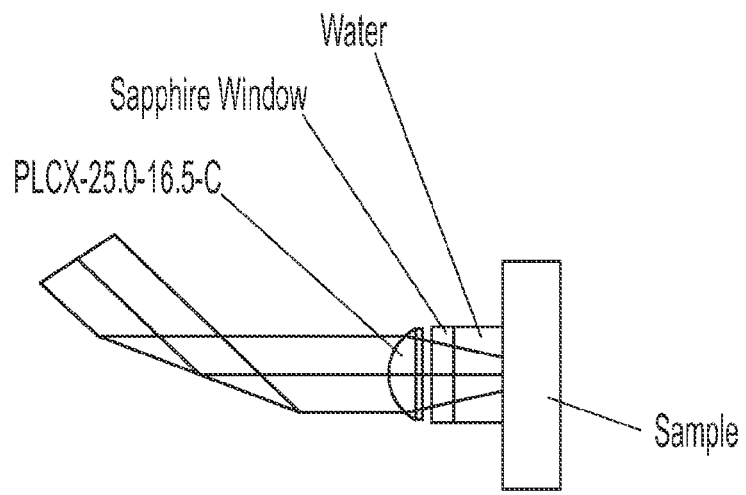
FIG. 14 is a view of a modification of the PH4 concept for a shorter water column.

Advanced process head designs were sought that would provide the best features of both of the process heads discussed above. First, improvements of the PH4 concept were investigated wherein the water column length was reduced to achieve higher laser pulse energy on the work surface. This was accomplished by using a shorter focal length final focusing lens followed by a window placed above the work surface to reduce the water column length to 10 mm. FIG. 14 presents a ray trace of the revised PH4 configuration for a short water column.

The geometry of FIG. 14 was tested in a prototype configuration with several thicknesses of sapphire window. In all cases, the shock wave generated in the water caused a fracture of the sapphire window at relatively low laser pulse energy levels. While a larger fraction of the laser output energy reached the work surface for this geometry than did in the original PH4 geometry (less water absorption), the fluence available at the work surface was still limited to about 15 J/cm$^2$.

Dual-Water-Film Concept

A second approach to an advanced process head that combines the benefits of both the PH4 and PH5 process heads is to generate a water film on the work surface for the confining overlay and a second water film on the sapphire window to continually wash paint debris and backsplash water droplets from the optical surface. The air gap between the two water films will prevent water borne shock waves from reaching the window and causing it to fracture. The main technical issues in this concept include:

generation of the water films in a compact process head;

beam distortion by water-film surface waves on the sapphire window; and possible window damage by high velocity water droplets.

Figure 15A:
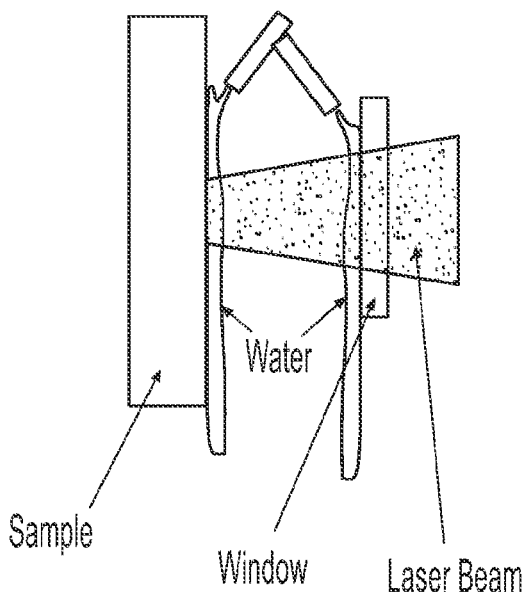
FIG. 15A is schematic view of a prototype arrangement for testing the dual-water-film concept.
Figure 15B:
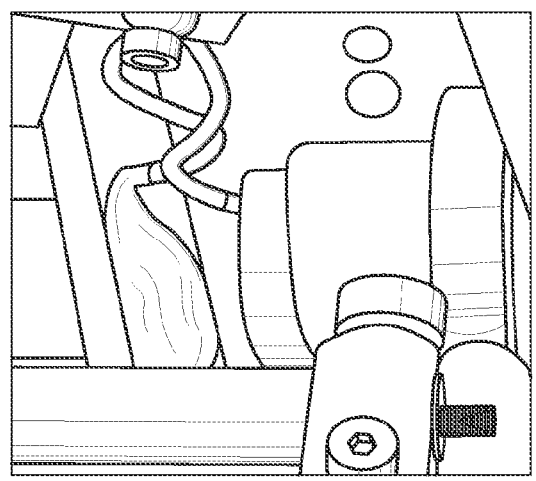
FIG. 15B is a view of a prototype arrangement for testing the dual-water-film concept.

The dual-water-film concept was tested in a prototype configuration as illustrated in FIGS. 15A and 15B.

A series of laser exposures was employed to assess the survivability of a 2.3-mm thick sapphire window in the dual-water-film geometry. A sequence of laser pulses at fixed energy was applied and the window was inspected at periodic intervals. The energy level was then raised and more pulses were applied. Table 1 summarizes the number of tests at each energy level for two different sapphire windows and a fused silica window (0.125-inch thick).

ever, eventually the window may be eroded, particularly at energies above 25 J. The fused silica did not exhibit pitting but fractured at high pulse energy. An alternative material, spinel (MgAl$_2$O$_4$), may be suitable as a window material.

Advanced Process Head Design

Figure 16:
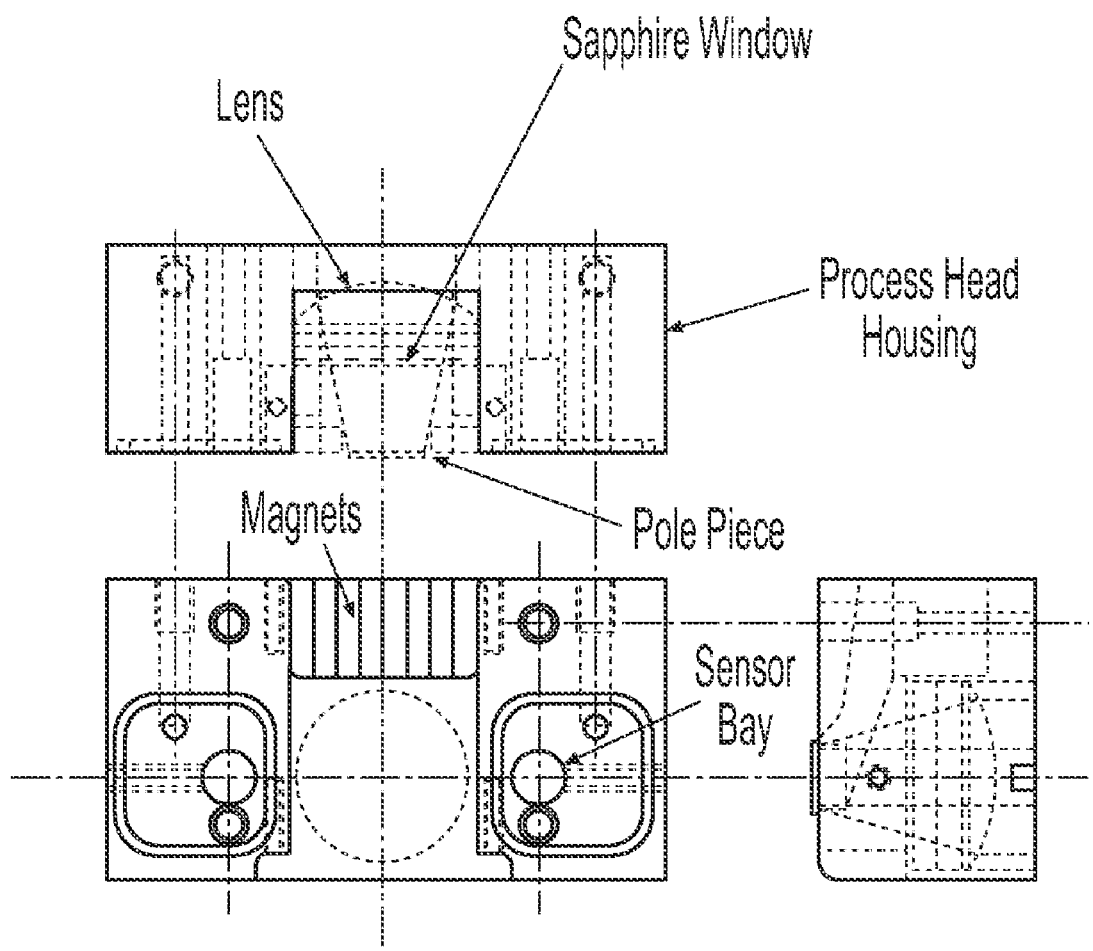
FIG. 16 is a layout drawing for dual-water-film process head faceplate (PH6).

Based on the preliminary results for the dual-water-film concept, a new process head was designed for installation on the articulated arm. A layout drawing for the process head faceplate is presented in FIG. 16. The faceplate is designed to be directly attached to the prism module of PH4, replacing the water column faceplate. Shown in the figure is the aluminum faceplate, the optics and beam path, and the magnets and pole pieces incorporated for front surface motion sensing. Miniature sensor coils were designed to fit into the sensor bay holes indicated in the figure. Not shown in the figure are means for delivering the water films to the work surface and sapphire surface.

Figure 17:
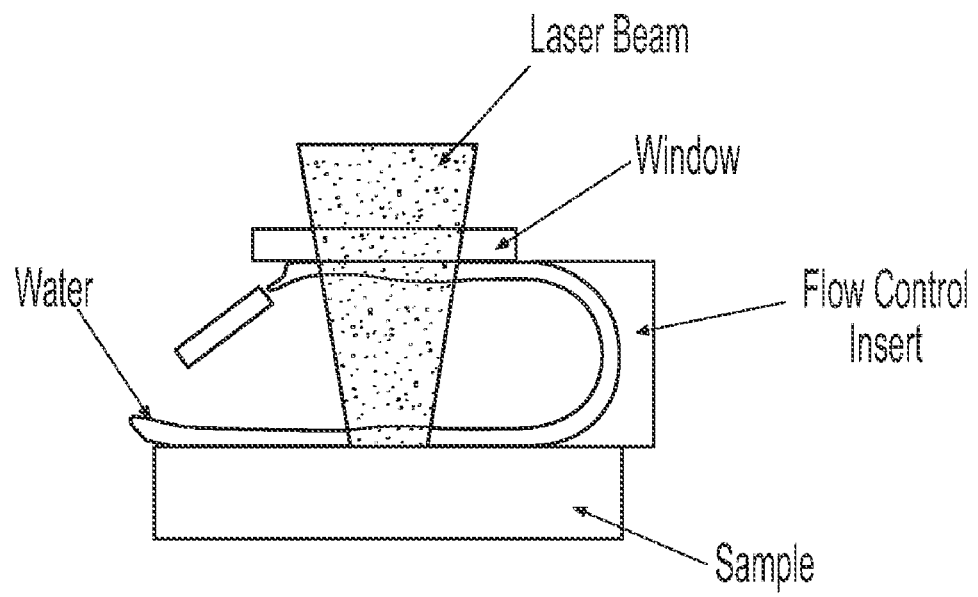
FIG. 17 is a view of a single water source geometry for a dual-water-film process head.
Figure 18:
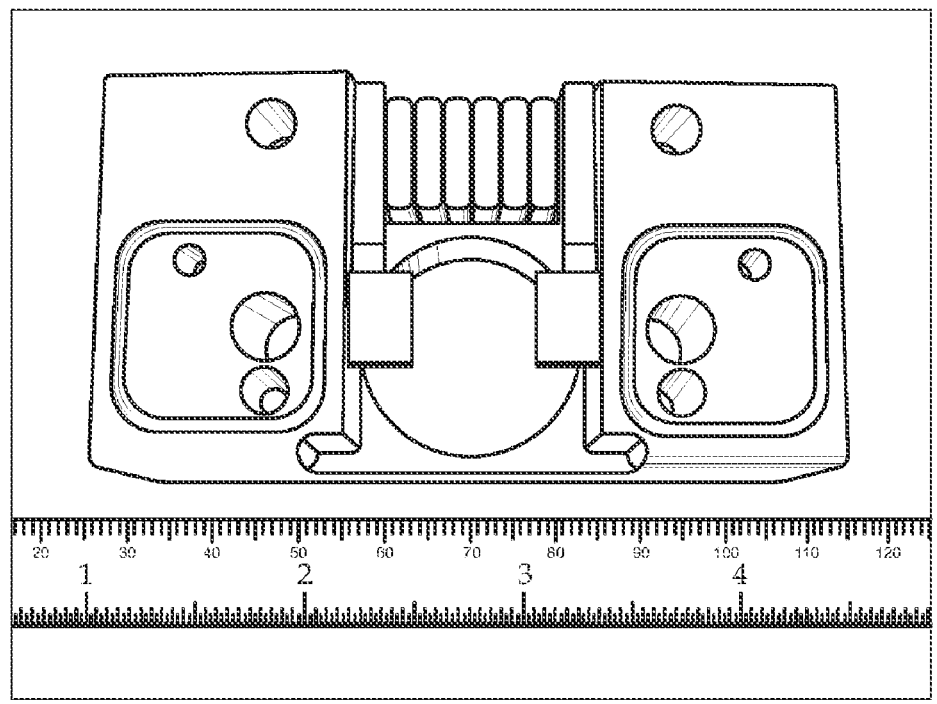
FIG. 18 is a view of a faceplate and magnet assembly.

Water delivery may be accomplished in the process head by using two or more sources (nozzles) as illustrated in FIGS. 15A and 15B. A simpler approach may be to use a single water nozzle in the process head and a means to redirect the flow from one film to form the second film. For example, the water film protecting the window could be redirected by a curved surface to form the confining overlay water film for stress wave generation. This concept is illustrated in FIG. 17. The PH6 faceplate and magnet assembly have been fabricated and are shown in the photograph of FIG. 18.

A critical feature of the PH6 process head is the incorporation of EMAT sensor technology for on-axis front-surface motion detection. The magnet assembly and pole pieces will provide a strong magnetic field parallel to the work surface. A special tape that has a conducting pattern of metal foil will be applied to the work surface. "Pi-Box" and "Pi-Rail" patterns discussed above will sense the out-of-plane motion of the surface. The foil patterns can be manually cut from adhesive-backed aluminum foil. Alternatively, a set of custom foil patterns can designed and then fabricated. For example, a manufacturer of flexible electronic circuits could be used to fabricate such foil patterns. These patterns are prototypes for "inspection tape" that could be used in implementation of the LBI process in production. The patterns are copper foil traces

TABLE 1

Window damage test results for dual-water-film geometry

| Pulse Energy (J) | Number of Pulses on Sapphire 1 | Damage on Sapphire 1 | Number of Pulses on Sapphire 2 | Damage on Sapphire 2 | Number of Pulses on Silica 1 | Damage on Silica 1 |
|---|---|---|---|---|---|---|
| 10 | 100 | None | 150 | None | 150 | None |
| 15 | 150 | None | 155 | None | 150 | None |
| 20 | 120 | None | 150 | None | 150 | None |
| 25 | 100 | Slight pitting outside beam | 125 | Slight pitting outside beam | 150 | None |
| 35 | 50 | More pitting | 65 | More pitting | 65 | Fracture |
| 42 | 50 | More pitting | 60 | More pitting | 30 | Shattered |

Figure 19:
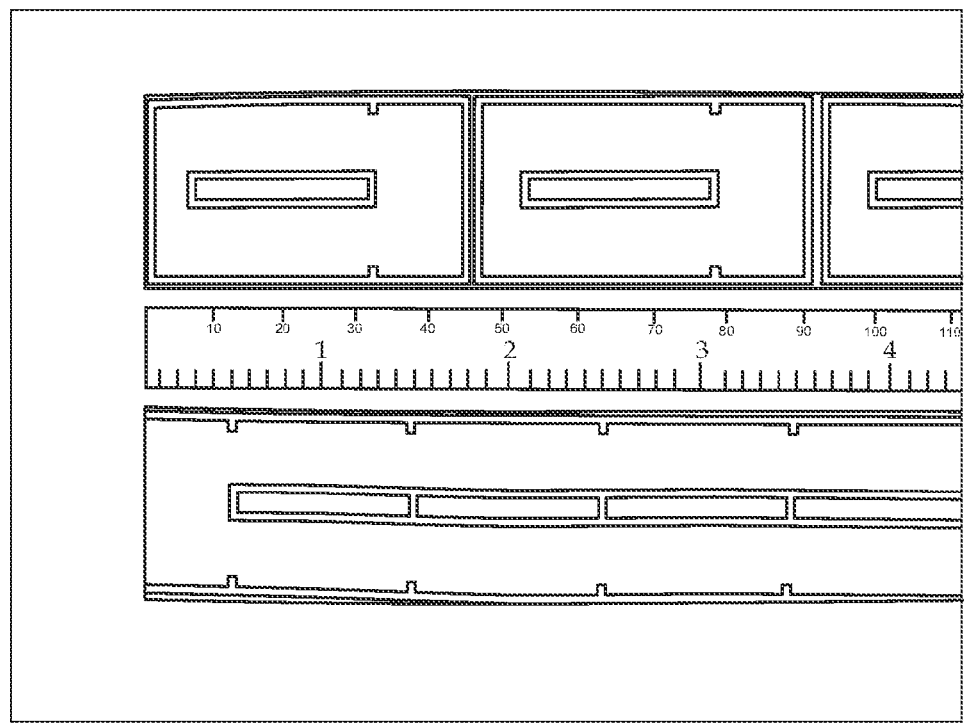
FIG. 19 is a view of pi-box and pi-rail prototype conducting patterns for EMAT sensing (copper on adhesive-backed Kapton).

The sapphire window survived for 100 pulses at 25 J per pulse (32 J/cm$^2$ on the work surface) with only minor pitting of the surface in an annular region outside the beam area. The cause of the pitting is not known, but may be due to high velocity impact of water droplets that penetrate the protective water film. The pitting does not affect beam delivery, howdeposited on Kapton film with an adhesive backing. No black absorbing film was incorporated in the prototype patterns, although this would be simple to add for production tape. FIG. 19 presents a photograph of the two prototype patterns.

In the pi-box patterns (rectangular loop pattern), the PH6 magnet provides a field that is perpendicular to the sensitive strip of the foil pattern (1 mm by 3 mm vertical strip located on the beam axis). Horizontal strips parallel to the magnetic field carry the current generated in the sensitive strip, therefore, surface motion in those regions does not contribute to signal current. The closing strip for the loop is well outside of the magnetic field concentrated by the pole pieces and also does not contribute to the signal. The spacing between the sensing strip and the closing strip (1 inch) is designed to be compatible with the spacing between the beam axis and the sensor bay in the process head. A small pickup coil will be placed in the sensor bay to sense the circulating current in the pattern loop. The pi-box pattern is designed for single point sensing applications, while the pi-rail is suitable for inspection at 1-inch intervals along a bonded joint. The principle of operation of the pi-rail is identical to that of the pi-box, however the current flows predominately in two loops instead of one (one loop on either side of the sensitive strip).

Figure 20:
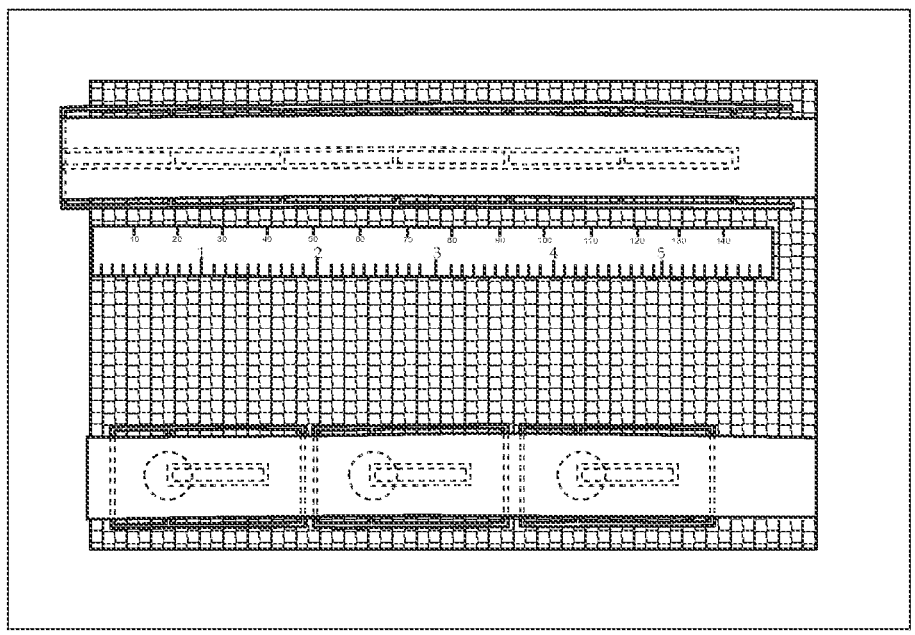
FIG. 20 is a view of pi-box and pi-rail prototype conducting patterns with black paint applied for front surface EMAT sensing.

The patterns shown in FIG. 19 have no absorbing layers to absorb the laser beam for stress wave generation. In testing the copper patterns, a flat black paint was applied to the pattern to absorb the laser light. FIG. 20 shows the appearance of a bonded composite sample with the patterns in place and a coating of flat black paint applied after the pattern was adhered to the sample front surface. In the production application, the "inspection tape" would be supplied with the absorbing coating already applied.

While this invention has been described as having an exemplary design, the present invention may be further modified within the spirit and scope of this disclosure. This application is therefore intended to cover any variations, uses, or adaptations of the invention using its general principles.

What is claimed is:

1. A system for non-destructive testing of a bond in a bonded article, the system comprising:
   a laser configured to direct laser pulses onto a first surface of the bonded article and thereby induce the generation of a compressive stress waves in the bonded article that travel through the bond, the laser being further configured to direct the laser pulses in a probe-break-probe inspection sequence comprising a first laser pulse having a first fluence, a second laser pulse having a second fluence which is greater than the first fluence but less than a fluence required to break the bond, and a third laser pulse having a fluence which is approximately the same as the first fluence;
   a gauge, at least a portion of the gauge being adjacent to a second surface of the bonded article;
   a sensing coil adjacent to the gauge; and
   a magnet capable of applying a magnetic field to the second surface.

2. The system of claim 1, wherein the sensing coil is inductively coupled to the gauge.

3. The system of claim 1, wherein the sensing coil is electrically connected to the gauge.

4. The system of claim 1, wherein the gauge comprises at least one of: a rectangular loop, aluminum tape, and a plurality of closed loops.

5. The system of claim 1, wherein the sensing coil is configured to detect a stress wave signature indicative of at least a partial failure of the bond.

6. The system of claim 5, further comprising a processor to determine a strength of the bond, using the stress wave signature.

7. The system of claim 1, wherein the system is mobile.

8. The system of claim 1, wherein each fluence is between about 15 J/cm$^2$ and about 40 J/cm$^2$.

9. The system of claim 1, wherein the first surface and the second surface are the same.

10. A system for non-destructive testing of a bond between a coating and a coated surface on a coated article, the system comprising:
    a laser configured to induce the generation of a compressive stress wave in the coated article, the laser further configured to direct laser pulses in a probe-break-probe inspection sequence at one or more locations on the coated article;
    a gauge, at least a portion of the gauge being adjacent to a surface of the coated article;
    a sensing coil adjacent to the gauge; and
    a magnet capable of applying a magnetic field to the surface.

11. The system of claim 10, wherein the sensing coil is at least one of inductively coupled to the gauge, and electrically connected to the gauge.

12. The system of claim 10, wherein the gauge comprises at least one of: a rectangular loop, aluminum tape, and a plurality of closed loops.

13. The system of claim 10, wherein the sensing coil is configured to detect a stress wave signature indicative of at least a partial failure of the bond.

14. The system of claim 10, wherein the probe-break-probe inspection sequence comprises a first laser pulse having a first fluence, a second laser pulse having a second fluence which is greater than the first fluence but less than a fluence required to break the bond, and a third laser pulse having a fluence which is approximately the same as the first fluence.

15. The system of claim 10, wherein the coated surface and the surface are the same.

* * * * *